United States Patent [19]

Colliopoulos et al.

[11] Patent Number: 4,548,806

[45] Date of Patent: * Oct. 22, 1985

[54] PSYLLIUM HYDROPHILIC MUCILLOID COMPOSITION

[75] Inventors: John A. Colliopoulos, Evanston; David B. Paul, Lake Zurich; James G. Young, Northbrook, all of Ill.

[73] Assignee: G. D. Searle & Co., Skokie, Ill.

[ * ] Notice: The portion of the term of this patent subsequent to Jul. 10, 2001 has been disclaimed.

[21] Appl. No.: 510,051

[22] Filed: Jul. 5, 1983

Related U.S. Application Data

[63] Continuation-in-part of Ser. No. 401,433, Jul. 23, 1982, Pat. No. 4,459,280.

[51] Int. Cl.[4] ................................................ A61K 9/00
[52] U.S. Cl. ........................................ 424/35; 514/23; 514/19
[58] Field of Search .................. 424/180, 361, 35, 177, 424/35; 514/23, 19

[56] References Cited

U.S. PATENT DOCUMENTS

| | | | |
|---|---|---|---|
| 3,455,714 | 7/1969 | Bishop et al. | 427/421 |
| 3,798,054 | 3/1974 | Kanata et al. | 424/35 |
| 3,882,228 | 5/1975 | Boncey et al. | 424/35 |
| 4,321,263 | 3/1982 | Powell et al. | 424/78 |

OTHER PUBLICATIONS

Forman et al., *Chemical Abstracts*, vol. 69, 1968, p. 2414, No. 25994q.

*Primary Examiner*—Johnnie R. Brown
*Assistant Examiner*—Elli Peselev
*Attorney, Agent, or Firm*—Steven M. Odre; John J. McDonnell

[57] ABSTRACT

This invention relates to a method of increasing the dispersibility and mixability of psyllium hydrophilic mucilloid by applying a film of hydrolyzed starch oligosaccharide, a mono-or di-saccharide, a polyglucose, or a polymaltose.

11 Claims, No Drawings

PSYLLIUM HYDROPHILIC MUCILLOID COMPOSITION

This application is a continuation-in-part of application Ser. No. 401,433 filed July 23, 1982, now U.S. Pat. No. 4,459,280.

BACKGROUND OF THE INVENTION (a) Field of the Invention

The present invention relates to a method for producing a psyllium hydrophilic mucilloid with improved dispersibility and mixability and the novel composition thereby produced. In its method aspect, it relates to a novel process comprising dissolving a hydrolyzed starch oligosaccharide, a mono- or di-saccharide, a polyglucose, or a polymaltose in a suitable solvent system and applying the system as a thin film on the mucilloid and then drying. Optionally, where appropriate, the solution contains a low-calorie sweetener and/or a flavoring agent. In its composition aspect, the invention relates to a novel composition comprising psyllium hydrophillic mucilloid coated with a thin film of a hydrolyzed starch oligosaccharide, a mono- or di-saccharide, a polyglucose, or a polymaltose.

Psyllium hydrophilic mucilloid consists of the mucilaginous portion (the husk either milled or unmilled) of blond psyllium seeds. Psyllium hydrophilic mucilloid contains natural mucillage and forms a gelatinous mass on contact with water. It is useful in the treatment of constipation by acting as a fecal softener and also as a demulcent in the presence of inflamed mucosa. Psyllium hydrophilic mucilloid, however, exhibits poor dispersability and mixability in water. The numerous individual particles tend to agglomerate when psyllium hydrophilic mucilloid is mixed with water. Hydration takes place over the surface of such agglomerated aggregates to form gel-coated lumps, the interiors of which are still substantially dry, and these lumps are extremely difficult to disperse. This effect is aggravated by the fact that psyllium has a tendency to float on the surface of the water, allowing partially dissolved particles to agglomerate into large masses. In addition, the taste of psyllium hydrophilic mucilloid is unacceptable to many persons.

One attempt at alleviating the problems has been to dry mix the psyllium hydrophilic mucilloid with a high percentage of a sugar (typically about 50%). The taste is improved slightly and dispersibility and mixability are moderately improved by the addition of a sugar. However, diabetics and people who are on restricted diets may have difficulty taking sugar-treated psyllium hydrophilic mucilloid due to the high sugar content (3.5 g–7.0 g about 14 to 28 calories per dose). In addition, the cost of raw materials, storage and processing is higher with the sugar added.

(b) Prior Art

Psyllium hydrophilic mucilloid in combination with a high concentration of a sugar is widely known and available commercially for use in treating constipation. See. e.g. Goodman and Gilman, *The Pharmacological Basis of Therapeutics* 4th Ed. pg 1026 (1970). Also in U.S. Pat. No. 3,455,714, a method is described for improving the dispersability and dissolution rate in water of water soluble gums using cellulose derivatives. U.S. Pat. No. 4,321,263 relates to increasing the dispersibility of pysllium hydrophilic mucilloid by wetting the psyllium particles with an alcoholic solution of polyethylene glycol and/or polyvinylpyrrolidone.

SUMMARY OF THE INVENTION

It is therefore an object of this invention to develop a psyllium hydrophilic mucilloid composition which is readily dispersible and mixable in aqueous solution. A further object of this invention is to develop a psyllium hydrophilic mucilloid which is more acceptable for diabetics and/or people on a restricted sugar diet yet still retain acceptable taste.

In accordance with these objects, it has been discovered that psyllium hydrophilic mucilloid agglomerated with a coating of a water soluble hydrolyzed starch oligosaccharide, a mono- or di-saccharide, a polyglucose, or a polymaltose has greatly improved dispersibility and mixability. In addition, since sugar is greatly reduced or in some cases even eliminated from the composition, the intake of pysllium hydrophilic mucilloid may not be restricted for diabetics, and intake for dietary purposes will become more acceptable because of the reduced or eliminated sugar. Acceptable taste may be maintained by the inclusion of a low calorie sweetener and/or flavor agent.

By coating the psyllium hydrophilic mucilloid with the water soluble hydrolyzed starch oligosaccharide, a mono- or di-saccharide, a polyglucose, or a polymaltose to form an agglomerate, water penetrates over the wider surface area of the individual particles rather than over an aggregate of particles, thus greatly increasing the dispersal and mixing rate. In addition, the presence of the water soluble coating aides in the dispersal and mixing.

The composition of the present invention is prepared by dissolving or dispersing a hydrolyzed starch oligosaccharide, a mono- or di-saccharide, a polyglucose, or a polymaltose in a suitable solvent system, the solution containing about 7 to about 18% or more solids. If inclusion of a low calorie sweetener and/or flavoring agent is desired, they can be added to the dry system, or to the solvent system. The solvent system is then sprayed or otherwise applied so that a thin film is developed over the psyllium hydrophilic mucilloid, followed by a short period of drying. The desired amount of coating may be added to the psyllium hydrophilic mucilloid by alternating the steps of applying the thin film and short periods of drying, thus building up the desired coat with a number of thin layers, this being preferred over one thick layer. The amount of coating is not critical to this invention but in general will be from about 3% to 11% of the final product. A preferred coating is 4 to 5 weight percent of the final product. The material is then dried in a conventional manner until the desired moisture content is attained. Bulk density in general will vary based on the technique and amounts used and is not critical to the invention, but a preferred bulk density is between about 0.25 g/ml and about 0.40 g/ml. The temperature of the coating media is not critical, the only possible consideration being that the coating material must remain substantially dissolved therein throughout the coating process. Likewise the coated psyllium hydrophilic mucilloid of this invention may be dried by conventional drying methods applicable to drying particulate material as long as the conditions are such that substantial degradation does not occur.

Starchs consist of granules separated from edible sources such as potato, arrowroot, oats, wheat, pea, bean, rice, corn, buckwheat, tapioca, rye or barley. A preferred source of starch is corn. The granules exist as a polymeric compound consisting of about 27% linear polymer (amylose) and 73% branched polymer (amylopectin), with these two polymers so associated in the crystal lattice that they are practically insoluble in cold water or alcohol. Starch is soluble in boiling water giving a colloidal solution which may form a jelly on cooling.

Hydrolysis of starch may be accomplished by reaction of either acid, enzymes (e.g. α-amylase, β-amylase or amyloglucosidase) or a combination of the two either together or reacted in series. The hydrolysis will follow different pathway depending on whether acids or enzymes are used. The result is a mixture of oligosaccharides which may be separated for their different properties. The resulting separated water soluble hydrolyzed starch oligosaccharides are classified by their reducing sugar content i.e., the mono- or di-saccharides such as glucose, or fructose. The percent reducing sugar content in the particular hydrolyzed starch oligosaccharide is measured on a weight/weight basis as the Dextrose Equivalent or D.E. Hydrolyzed starch oligosaccharides with a D.E. of from zero to 20 are called maltodextrins. The solid malto dextrins have low to moderate sweeteness, low to moderate hygroscopicity, solubility in water and alcohol, and have reduced browning. Above a DE of about 20 the hydrolyzed starch oligosaccharides are called syrup solids. These syrup solids are soluble but have a more noticable sweetness and are more hygroscopic. Above a D.E. of about 30, the syrup solids become unacceptable for use in the invention. First, the calories added by the mono- and di-saccharides begin to outweigh the advantages gained by the elimination of sugar. Second, the syrup solids with D.E.'s above 30 become so hygroscopic that the consistency, i.e., too much water, is unworkable. A preferred water soluble hydrolyzed starch oligosaccharide has a DE of 0–30. A preferred maltodextrin has a DE of about 10 ie. a reducing sugar content ratio of 10% w/w of the oligosaccharide.

The mono-saccharides are those carbohydrates that in general are aldehyde-alcohols or ketone alcohols that are a hexose or pentose and have a sweet taste. They are readily soluble in water and form crystalline solids. Examples of the mono-saccharides are dextrose, mannose and fructose.

The di-saccharides are those carbohydrates which yield 2 mono-saccharides on hydrolysis. Examples of di-saccharides are lactose, sucrose and maltose.

Polyglucose and polymaltose are those compounds exemplified by U.S. Pat. Nos. 3,766,165 and 3,876,794, incorporated herein by reference. A commercial available preparation of a polyglucose is called polydextrose and has a low calorie content (1 Kcal/g) and little or no sweetness. It is primarily used as a low calorie, bulk replacement for sugar in foodstuffs. Polydextrose is a partially metabolizeable, water-soluble polymer prepared by the condensation of a melt which consists of approximately about 89% D-glucose, about 10% sorbitol and about 1% citric acid on a weight basis.

Suitable solvent systems include those pharmacologically acceptable solvents of the hydrolyzed starch oligosaccharides mono- or di-saccharide, the polyglucoses, and polymaltoses, such as alcohol and water. A preferred solvent system is water.

The inclusion of a sweetening agent should be limited to low calorie sweetening agents that add sweetness without substantial bulk. Examples of such sweeteners are, but not limited to, saccharin, cyclamate and the dipeptide sweeteners such as set forth in U.S. Pat. Nos. 3,475,403, 3,492,131, and 4,029,701 and the like. These sweeteners may be used alone or in combination with one another. Most suitable among these compounds is the methyl ester of α-L-aspartyl-L-phenylalanine (aspartame or APM).

Flavoring agents such as certain volatile oils or other liquid or dry agents which are pharmacologically acceptable may also be incorporated in the composition. Examples of flavoring agents are orange, strawberry and cherry.

The film may be applied by any convenient technology. A preferred method of agglomerating the psyllium hydrophilic mucilloid is by fluid bed agglomeration. Finally, the material may be dried by conventional hot air means; such as fluid bed drying or tray drying. A preferred method of drying is fluid bed drying. The result of this process is a material that has a low bulk density, preferably in the range of about 0.25 g/ml to about 2.40 g/ml, where each rounded teaspoon will deliver in the area of 3.5 g of psyllium hydrophilic mucilloid, has a caloric content of about 2 calories per dose and exhibits greatly improved dispersibility and mixability. In addition, the product surprisingly has improved flow and a more uniform appearance when compared to previous compositions. The improved flow greatly aids in the packaging of the composition.

DESCRIPTION OF THE PREFERRED EMBODIMENTS

The following examples further illustrate details for the preparation of the composition of the invention. The invention which is fully set forth in the foregoing disclosure, is not to be construed as being limited either in spirit or scope by these examples. Those skilled in the art will readily understand that known variations and the conditions and processes of the following preparation procedures exists.

EXAMPLE 1

Into a Freund Flo Coater was placed 38.0 Kg of sized psyllium hydrophilic mucilloid. Separately a solution of 2.0 Kg of maltrin M-100 (maltodextrin DE 10% w/w) and 0.06 Kg of sodium saccharin was dissolved in 28 liters of water. The psyllium hydrophilic mucilloid was alternately sprayed with the solution, and dried. Finally, the husk composition was fluid bed dried until the composition had a density of 0.33 g/ml and a rounded teaspoon contained 3.9 g, 3.5 g of which were psyllium hydrophilic mucilloid.

EXAMPLE 2

Using the method of Example 1 the following sweeteners and amounts were used in preparation of psyllium hydrophilic mucilloid compositions.

| | |
|---|---|
| Sodium Saccharin | 0.14–0.17% |
| APM | 0.25% |
| Ca cyclamate & Na cyclamate | 0.6% each |

EXAMPLE 3

Using an agglomerator of the type described in U.S. Pat. No. 2,995,773, an agglomerated psyllium hydrophilic mucilloid composition can be prepared.

EXAMPLE 4

Using the method of Example 1, further compositions were made with flavoring agents (orange and cherry) and without flavoring agents. Those products that are flavored had a bulk density of between about 0.25 g/ml and about 0.35 g/ml while the unflavored products bulk density was between about 0.30 g/ml and 0.40 g/ml.

EXAMPLE 5

Using the method of Example 1, the following may be substituted for a hydrolyzed starch oligosaccharide.
dextrose
Polydextrose
glucose
fructose
mannose
lactose
sucrose
maltose

What is claimed is:

1. A composition having improved dispersability and mixability in water consisting essentially of psyllium hydrophilic mucilloid having a water-soluble coating from at least about 3% by weight of the composition, selected from the group consisting of a hydrolyzed starch ogligosaccharide having a D.E. of from Zero to 30, a mono-or disaccharide, a polyglucose or a polymatose and sweetened with aspartame, saccharin, cyclamate or a combination thereof, and wherein the composition has a bulk density of from about 0.25 g/ml to about 0.40 g/ml.

2. A composition according to claim 1 wherein the coating is from about 3% to about 11% by weight of the composition.

3. A composition according to claim 2 wherein the coating is a mono- or di-saccharide.

4. A composition according to claim 3 wherein the coating is sucrose or dextrose.

5. A composition according to claim 2 wherein the coating is a polyglucose or a polymaltose.

6. A composition according to claim 5 wherein the coating is a polyglucose which comprises about 89 weight percent D-glucose, about 10 weight percent sorbitol and about 1 weight percent citric acid.

7. A composition according to claim 1 wherein the water soluble hydrolyzed starch oligosaccharide is a maltodextrin having a D.E. of from zero to 20.

8. A composition according to claim 7 wherein the maltodextrin has a D.E. of 10.

9. A composition according to claim 1 wherein the water soluble hydrolyzed starch oligosaccharide is a syrup solid having a D.E. of from 20 to 30.

10. A composition according to claim 1 wherein a flavoring agent is added.

11. A composition according to claim 1 wherein the sweetener is aspartame.

* * * * *